(12) United States Patent
Anderson et al.

(10) Patent No.: US 9,347,859 B2
(45) Date of Patent: May 24, 2016

(54) ACTIVE FLUID SAMPLING FROM PISTON TOP LAND CREVICE OF PISTON ENGINE

(71) Applicant: Southwest Research Institute, San Antonio, TX (US)

(72) Inventors: Garrett L. Anderson, Seguin, TX (US); Robert R. Pool, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 312 days.

(21) Appl. No.: 14/103,997

(22) Filed: Dec. 12, 2013

(65) Prior Publication Data

US 2015/0168273 A1  Jun. 18, 2015

(51) Int. Cl.
*G01N 1/22*  (2006.01)

(52) U.S. Cl.
CPC .............. *G01N 1/22* (2013.01); *G01N 1/2226* (2013.01)

(58) Field of Classification Search
USPC .......................................... 73/862.72, 862.73
See application file for complete search history.

(56) References Cited

U.S. PATENT DOCUMENTS

| | | | | |
|---|---|---|---|---|
| 4,970,904 A | * | 11/1990 | Knotts | B60C 29/06 137/231 |
| 5,005,375 A | * | 4/1991 | Manz | B60H 1/00571 137/231 |
| 5,248,125 A | * | 9/1993 | Fritch | F16L 29/04 137/614.02 |
| 5,633,459 A | * | 5/1997 | Rodriguez | G01M 13/005 73/114.78 |
| 6,360,619 B1 | * | 3/2002 | Schultz, Jr. | F17D 3/10 137/613 |

* cited by examiner

*Primary Examiner* — Hezron E Williams
*Assistant Examiner* — Mark A Shabman
(74) *Attorney, Agent, or Firm* — Livingston Law Firm

(57) ABSTRACT

A system and method for sampling fluid from a top land piston crevice of a reciprocating piston engine. Access into the crevice is via a bore through the piston wall. A collector receives sampled fluid from the piston crevice, and has a housing, a valve, and a shuttle. The housing is an elongated hollow shell having a bore through its length, with the bore containing the valve and the shuttle. The valve opens to allow sampled fluid to pass along the bore toward the shuttle, when the valve is in an open position. The shuttle serves two purposes: it moves back and forth within the bore, thereby opening the valve, and also provides passages for storing sampled fluid within the housing.

14 Claims, 4 Drawing Sheets

US 9,347,859 B2

ACTIVE FLUID SAMPLING FROM PISTON TOP LAND CREVICE OF PISTON ENGINE

TECHNICAL FIELD OF THE INVENTION

This invention relates to testing internal combustion engines (and other piston engines), and more particularly to sampling fluid from the top land crevice of a piston.

BACKGROUND OF THE INVENTION

Crevices in the combustion chambers of piston engines are of interest to researchers for many reasons. As one example, combustion chamber crevices in internal combustion engines are significant contributors of hydrocarbon (HC) emissions. These crevices are identified as narrow regions of the combustion chamber into which the combustion flame does not reach. One such crevice is the gap between the piston and the cylinder wall. During the compression stroke, unburned charge is pushed into this crevice. The crevice is narrow enough to quench the flame front, leaving unburnt gases, so that during the power stroke, as the piston descends and the exhaust valve opens, these unburnt gases re-emerge in the exhaust.

To successfully achieve emissions goals, engine design and operation must account for the effects of combustion chamber crevices. To this end, efforts have been made to sample material in the piston crevices. Past sampling methods involve drawing the sample out through tubing connected to a hole through the piston near the piston rings. The tubing traverses the connecting rod and is carried by a specially designed linkage to the point where it exits the crankcase.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to sampling the fluid that collects in piston top land crevices of reciprocating engines. Interest in this topic has increased in recent years due to low speed pre-ignition problems common in high-BMEP gasoline engines. Past sampling methods have been unsuccessful in collecting and preserving a sample of fluid suitable for fully understanding the composition of the crevice fluid.

The system and method described herein are particularly suitable for sampling piston crevices of internal combustion engines, but would be suitable for other piston engines. The method may be performed while the engine is in normal operation. The sampling system and method are particularly compatible with automotive engine architecture, but can be used with any piston engine of any thermodynamic cycle or fuel type.

Figure 1:
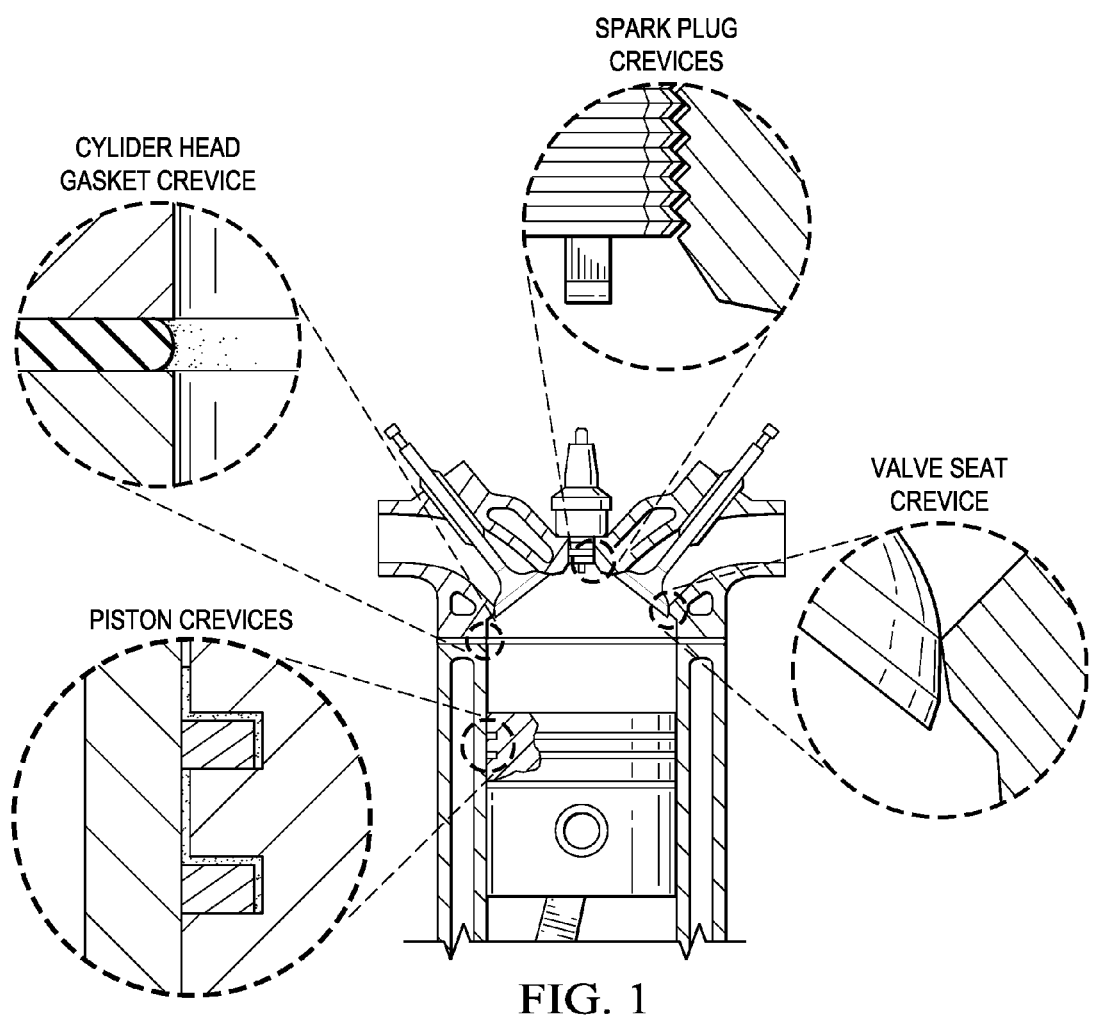
FIG. 1 illustrates various combustion chamber crevices.

FIG. 1 illustrates various combustion chamber crevices of an internal combustion engine. Specific examples of combustion chamber crevices are: the piston crevices, consisting of the top-land volume, the volume within the top-ring groove not occupied by the ring and the volume between the compression rings; the cylinder head gasket crevice; the valve seat crevice; and spark plug crevices.

Figure 2:
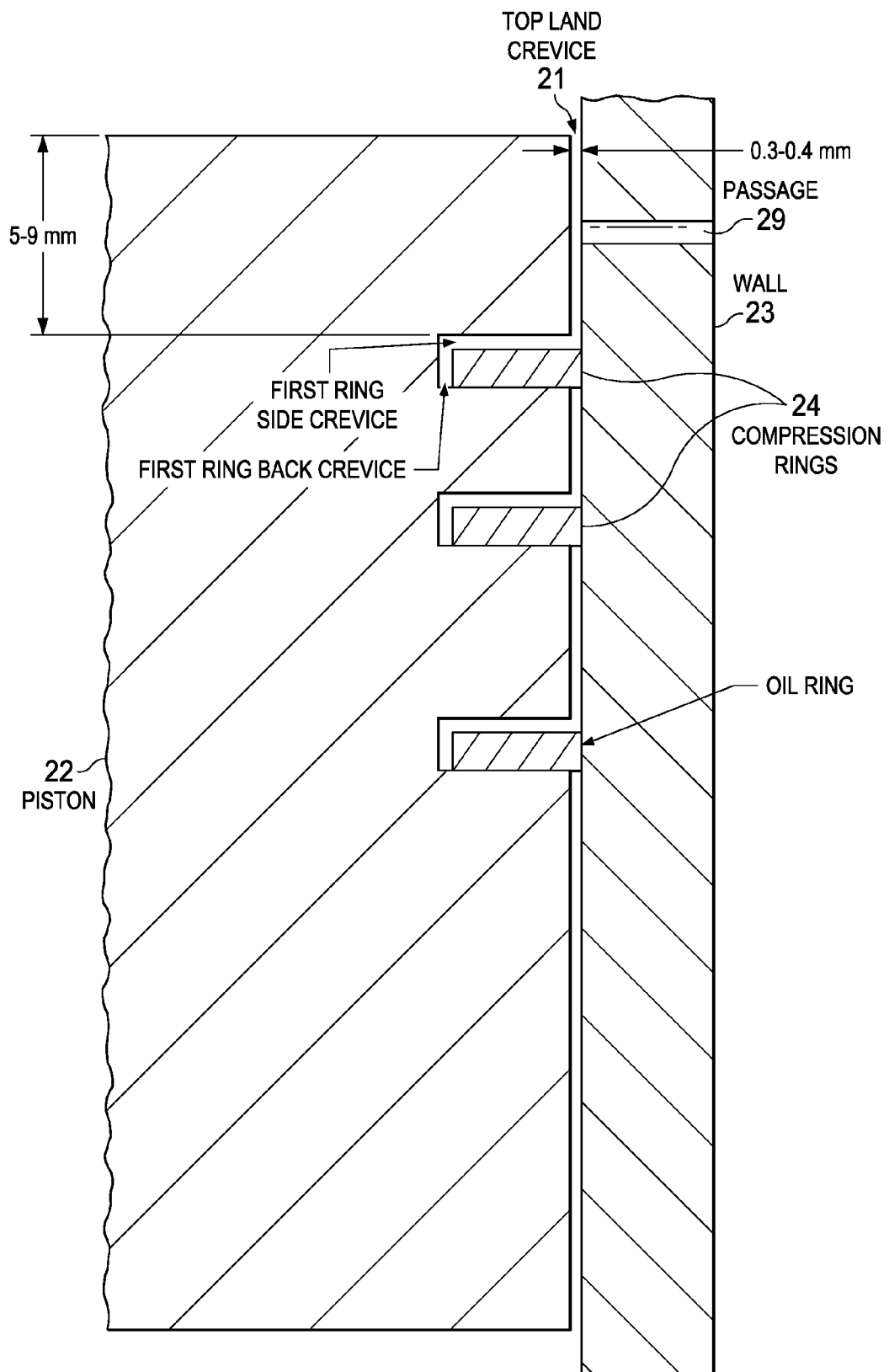
FIG. 2 illustrates the piston crevices of FIG. 1 in further detail.

FIG. 2 illustrates the top land piston crevice 21, which is the crevice sampled by the system and method described herein. It is an area between the piston 22 and the piston liner 23 above the top compression ring 24. Fluid sampled from the top land crevice 21 may also include fluid from the first ring side and back crevice areas. For purposes of this description, all sampled fluids are included in the term "top land crevice" fluids. FIG. 2 also illustrates typical dimensions (height and width) of the top land crevice in an automotive engine.

A passage 29 through the cylinder wall 23 provides access into the top land crevice 21 for the sampling device described below. The cylinder "wall" may be the engine block or engine block with a cylinder liner.

Figure 3:
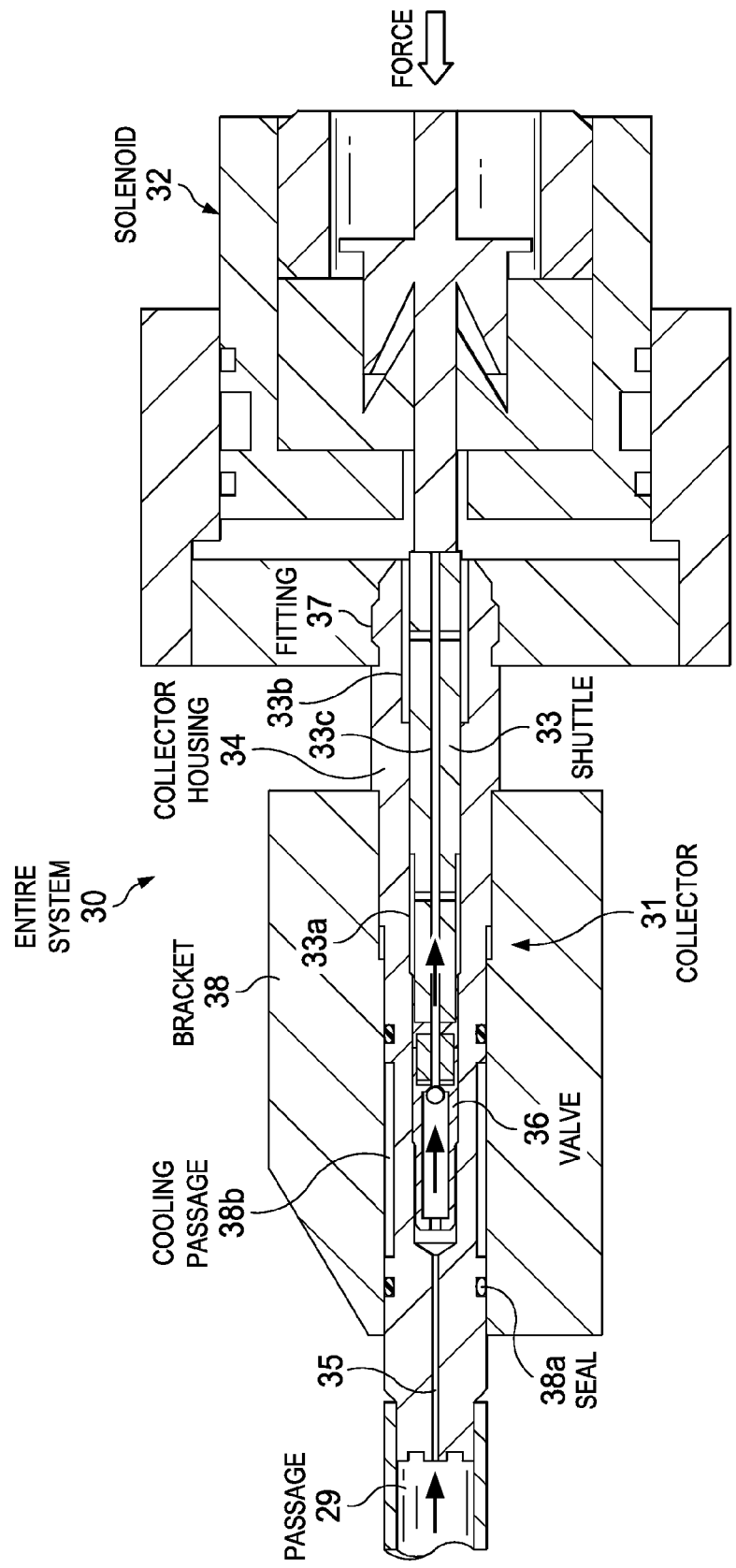
FIG. 3 illustrates a system for sampling the top land crevice of a piston.

FIG. 3 illustrates a piston top land crevice sampling system 30. System 30 samples fluid from the top land crevice proximate to a piston 22 of a piston engine. For example, the piston top land crevice could be the crevice 21 shown in FIG. 2 in an internal combustion engine.

Referring to both FIGS. 2 and 3, the sampling system 30 accesses the top land crevice 21 from outside the engine through a passage 29 through the cylinder wall (engine block and cylinder liner, if present). This passage 29 may be drilled and may be of very small size.

Sampling system 30 has two main parts: a collector 31 and a solenoid 32. As explained below, collector 31 contains a check valve 36. Solenoid 32 actuates the valve 36 by applying a force to a shuttle 33 that translates the force to the valve 36 to cause valve 36 to open when sampling is desired.

More specifically, collector 31 has an elongated housing 34. Housing 34 is conveniently cylindrical, but other geometries may be suitable. A bore 35 through the length of housing 34 is of varying diameters, and provides a fluid flow passage from a receiving end to an exit end of housing 34. Fluid from the crevice 21 enters the bore 35 at the receiving end of bore 35. When valve 36 is open, this fluid passes through valve 36 and toward the exit end of bore 35. When valve 36 is closed, flow is prevented from exiting the engine.

The receiving end of bore 35 is intended for fluid communication of fluid from the crevice 21 via passage 29. As explained below, the connection between the receiving end of bore 35 and passage 29 may be achieved in various ways. For example, the receiving end of housing 34 may be placed into passage 29. In general, a direct connection is desirable, such that bore 35 abuts with and is aligned with passage 29. Typically, this results in sampling system 30 having a horizontal orientation as shown in FIG. 3.

A next portion of bore 35 is typically of wider diameter and contains a check valve 36. A next portion of bore 35 contains shuttle 33.

Figure 4:
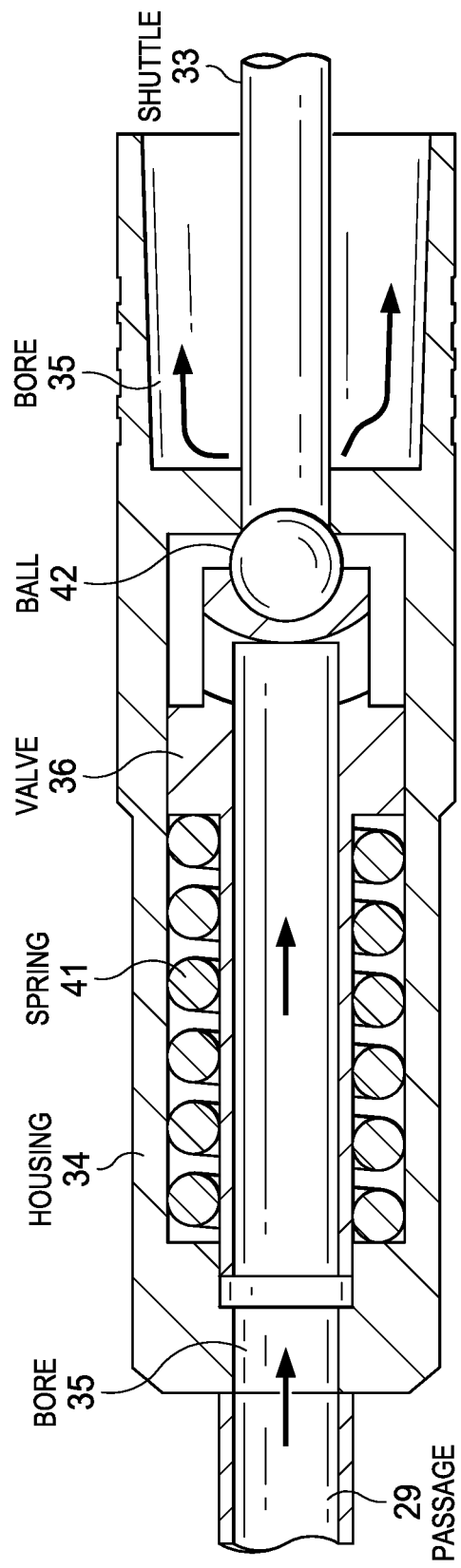
FIG. 4 illustrates the check valve of FIG. 3 in further detail.

FIG. 4 illustrates check valve 36 in further detail. Valve 36 is normally closed when a force from solenoid 32 is not applied. The flow pressure of gases out of the engine into bore 35 and toward valve 36 causes valve 36 to close. Also, a spring 41 within valve 36 biases the valve to a closed position. The strength of spring 41 can be adjusted if necessary to ensure that valve 36 closes when desired.

When closed, valve 36 provides a positive seal against cylinder pressure. This prevents combustion gases from leaking into the sampling system. Also, as explained below, because valve 36 is normally closed, collector 31 and/or shuttle 33 may be removed for purposes of removing sampled fluid without loss of fluid from the receiving end of bore 35.

Referring to both FIGS. 3 and 4, shuttle 33 translates force from the distal end of solenoid 32 to valve 36. This displaces ball 42 from its seated (closed) position to its open position. The opening of valve 36 allows fluid to flow past the ball 42 into the next portion of bore 35, that is, toward the exit end of housing 34.

The outer diameter of shuttle 33 is smaller than the inner diameter of housing 34 in those parts of bore 35 that contain shuttle 33. This allows shuttle 33 to move back and forth within bore 35 in response to force applied by solenoid 32. At least a portion of shuttle 33 is a close fit to bore 35 so that the reciprocating motion of shuttle 33 remains stable and linear.

Shuttle 33 stores sampled fluid within housing 34, either around its outer diameter or within inner passages or both. As explained below, after sampling, collector 31 is removable, and transportable. Also, regardless of whether the entire collector 31 is removed, if desired for removal of the sampled fluid, shuttle 33 may be removed from housing 34.

Some portions of shuttle 33 may have an outer diameter slightly smaller than other portions to allow fluid to collect within bore 35 around the outer surface of shuttle 33 when valve 36 is opened. In FIG. 3, shuttle 33 has two such portions with smaller outer diameters, identified as 33a and 33b. An additional benefit of this configuration of shuttle 33 is that it results in shuttle 33 being self-lubricating.

An additional storage area for sampled fluid may be provided if the diameter of shuttle 33 is decreased at the end proximate to, and at which it contacts, valve 36.

In addition, or alternatively, at least one passage 33c may be drilled along the length of shuttle 33, with cross drillings to the outer surface of shuttle 33. These passages 33c contain sample fluid collected within bore 35 between the outer surface of shuttle 33 and the inner surface of housing 34.

As illustrated in FIG. 3, in one embodiment, collector 31 may be installed in a holder or bracket proximate the cylinder wall (or engine block). Preferably, collector 31 is detachable from its connection to the passage 29, and easily removed after sampling. In the embodiment of FIG. 3, collector 31 is inserted into a hollow bore of a bracket 38, with a seal 38a near its receiving end, and a cooling passage 38b around its outer diameter.

Solenoid 32 may be any one of various types of linear actuators. Solenoids of suitable size and other specifications are commercially available. Solenoid 32 is just one example of various actuators that may be used to cause shuttle 33 to move back and forth. Another example of a linear actuator is a piezoelectric stack. It is also possible that shuttle 33 could be manually operated, with no need for a mechanical actuator.

In operation, sampling system 30, specifically the receiving end of bore 35, is in fluid communication with crevice 21 via passage 29. Solenoid 32 is used to open valve 36, which causes fluid from the piston crevice to enter bore 35, to pass through valve 36 and to collect within and around shuttle 33.

Sampling system 30 can be used to sample fluid at any time during the engine cycle and throughout the entire engine cycle if desired. Because valve 36 is actively opened by solenoid 32 and is not dependent on engine pressure, samples can be obtained whenever desired. Typically, sampling will be performed when the piston is at TDC of its compression stroke.

The "open" or "closed" state of sampling system 30 can be easily monitored. Because shuttle 33, which moves back and forth to actuate check valve 36, extends through collector 31, a position sensor can be used to detect changes in position of shuttle 33.

A feature of sampling system 30 is that collector 31 may be easily detached from the rest of the sampling system 30. After valve 36 has been opened a desired number of times or for a desired length of time, sampled fluid from the piston crevice will have collected within and/or around shuttle 33 and within housing 34. Solenoid 32 may be detached from collector 31, and collector 31 disconnected from its connection to passage 29. In this manner, collector 31, now containing sampled fluid, may be detached and transported to sample testing equipment.

Various means may be used to empty collector 31 of the sampled fluid, depending on the amount and viscosity of the sampled fluid. In some cases, collector 31 may simply be turned upside down (with the receiving end of bore 35 facing upward) so that gravity causes the sampled fluid to flow out of the space between shuttle 33 and housing 34 and from any passages within shuttle 33. In other cases, various solvents may be used to flush the sampled fluid out of the collector 31. Also, as stated above, shuttle 33 may be slid out of bore 35 and sampled fluid on or in shuttle 33 may then be removed.

A further feature of sampling system 30 is that it provides a means for adding fluid material into the engine via passage 29. As stated above, solenoid 32 is removable from collector 31. Now, shuttle 33 may be slid from bore 35. The collector 31, minus shuttle 33, remains in fluid connection to the cylinder via passage 29. Fitting 37 at the end of collector 31 may be used to attach a pump or other means of delivering fluid material into collector 31. This feature of the sampling system allows study of the effects of various chemicals in the cylinder.

What is claimed is:

1. A system for sampling fluid from a top land piston crevice of a reciprocating piston engine, during operation of the engine, comprising:
    a collector having a receiving end operable to receive sampled fluid from the piston crevice;
    wherein the collector comprises a housing, a valve, and a shuttle;
    wherein the housing is an elongated hollow shell having a bore through its length;
    wherein the bore contains the valve and the shuttle and communicates the sampled fluid from the receiving end of the housing to the valve;
    wherein the valve is operable to allow the sampled fluid to pass along the bore toward the shuttle when the valve is in an open position;
    wherein the shuttle is operable to move back and forth within the bore, thereby opening the valve, and to further store sampled fluid within its interior or between at least some of its exterior surface and the interior surface of the housing; and
    an actuator operable to move the shuttle back and forth within the bore.

2. The system of claim 1, wherein the shuttle has a reduced outer diameter along portions of its length for storing sampled fluid.

3. The system of claim 1, wherein the shuttle has passages in its interior for storing sampled fluid.

4. The system of claim 1, wherein the actuator is a solenoid.

5. The system of claim 1, wherein the collector is removably attached to a passage from the piston crevice.

6. The system of claim 1, wherein the shuttle is removable from the housing.

7. A method of sampling fluid from a piston top land crevice of a reciprocating engine, comprising:
    providing a passage into the crevice;
    attaching a collector to the passage, the collector having a receiving end operable to receive sampled fluid from the piston crevice via the passage;

wherein the collector comprises a housing, a valve, and a shuttle;

wherein the housing is an elongated hollow shell having a bore through its length;

wherein the bore contains the valve and the shuttle and communicates the sampled fluid from the receiving end of the housing to the valve;

wherein the valve is operable to allow the sampled fluid to pass along the bore toward the shuttle when the valve is in an open position;

actuating the shuttle to move back and forth within the bore, thereby opening the valve and causing fluid to collect within the housing in or around the shuttle.

8. The method of claim 7, further comprising repeating the actuating step until a desired amount of sampled fluid has been collected.

9. The method of claim 7, wherein the shuttle has a reduced outer diameter along portions of its length for storing sampled fluid.

10. The method of claim 7, wherein the shuttle has passages in its interior for storing sampled fluid.

11. The method of claim 7, wherein the actuating step is performed with a mechanical actuator.

12. The method of claim 11, wherein the actuator is a solenoid.

13. The method of claim 7, further comprising, after the actuating step has been performed one or more times, removing the collector from its attachment to the passage.

14. The method of claim 7, further comprising, after the actuating step has been performed one or more times, removing the shuttle from the housing and collecting the sampled fluid.

* * * * *